United States Patent
Bass et al.

(10) Patent No.: US 7,368,534 B2
(45) Date of Patent: May 6, 2008

(54) MYOSTATIN AND MIMETICS THEREOF

(75) Inventors: James Johnston Bass, Hamilton (NZ); Carole J. Berry, Hamilton (NZ); Ravi Kambadur, Hamilton (NZ); Mridula Sharma, Hamilton (NZ); Mark F. Thomas, Hamilton (NZ)

(73) Assignee: Orico Limited, Dunedin (NZ)

( * ) Notice: Subject to any disclaimer, the term of this patent is extended or adjusted under 35 U.S.C. 154(b) by 0 days.

(21) Appl. No.: 10/181,545

(22) PCT Filed: Jan. 18, 2001

(86) PCT No.: PCT/NZ01/00005

§ 371 (c)(1), (2), (4) Date: Nov. 20, 2002

(87) PCT Pub. No.: WO01/53350

PCT Pub. Date: Jul. 26, 2001

(65) Prior Publication Data

US 2003/0140356 A1 Jul. 24, 2003

(30) Foreign Application Priority Data

Jan. 18, 2001 (NZ) .................................. 502389

(51) Int. Cl.
C07K 14/00 (2006.01)
(52) U.S. Cl. .......................................... 530/350; 514/2
(58) Field of Classification Search ................ 530/350, 530/402
See application file for complete search history.

(56) References Cited

FOREIGN PATENT DOCUMENTS

| WO | WO 98/33887 A | 8/1998 |
|---|---|---|
| WO | WO 99/06559 A | 2/1999 |
| WO | WO 99/40181 A | 8/1999 |
| WO | WO 99/42573 A | 8/1999 |

OTHER PUBLICATIONS

Verma et al. (1997, Nature, vol. 389, pp. 239-242).*
Anderson et al.(1998, Nature, vol. 392, pp. 25-30).*
Palu et al.(1999, Journal of Biotechnology, vol. 68, pp. 1-13).*
Sigmund, C.D. 2000. Arterioscler Thromb Vasc Biol.20:1425-1429.*
Wall, R.J. 1996. Theriogenology 45:57-68.*
Jacks et al. (1992) Nature vol. 359, pp. 295-300.*
Chorev, M. et al., 1993 "A Dozen Years of Retro-Inverso Peptidomimetics" *Acc. Chem. Res.*, 26:266-273.
Freidinger, R.M et al., 1982 "Protected Lactam-Bridged Dipeptides for Use as Conformational Constraints in Peptides" *J. Org. Chem.*, 47:104-109.
Gonzales-Cadavid N.F. et al., 1998 "Organization of the human myostatin gene and expression in healthy men and HIV-infected men with muscle wasting" *PNAS USA* 95:14938-14943.
Grobet L., et al., 1997 "A deletion in the bovine myostatin gene causes the double-muscled phenotype in cattle" *Nature Genetics* 17:71-74.
Gyuris J., et al., 1993 "Cdi1, a human G1 and S phase protein phosphatase that associates with Cdk2" *Cell* 75:791-803.
Hogan, J.C. Jr., 1997 "Combinatorial chemistry in drug discovery" *Nature Biotechnology*, 15:328-330.
Ji S., et al., 1998 "Myostatin expression in porcine tissues: tissue specificity and developmental and postnatal regulation" *Am. J Physiol.* 275:R1265-R1273.
Kambadur R., et al., 1997 "Mutations in myostatin (GDF8) in double-muscled Belgian Blue and Piedmontese cattle" *Genome Res* 7:910.
L'Huillier P.J., et al., 1996 "Efficient and specific ribozyme-mediated reduction of bovine α-lactalbumin expression in double transgenic mice" *PNAS USA* 93:6698-6703.
McPherron A.C. & Lee S.J. 1997 "Double muscling in cattle due to mutations in the myostatin gene" *PNAS USA* 94:12457-12461.
McPherron A.C. et al., 1997 "Regulation of skeletal muscle mass in mice by a new TGF-beta superfamily member" *Nature* 387:83-90.
Nagai, U. et al., 1985 "Synthesis of a Bicyclic Dipeptide with the Sahpe of β-Turn Central Part" *Tetrahedron Letters* 26: 647-650.
Olson et al., 1993 "Concepts and Progress in the Development of Peptide Mimetics" *J. Med. Chem.*, 36:3039-3049.
Sharma M., et al., 1999 Myostatin, a transforming growth factor-β superfamily member, is expressed in heart muscle and is upregulated in cardiomyocytes after infarct. *J Cell Physiol* 180:1-9.
Smythe, M.L., et al., 1994 "Design and Synthesis of a Biologically Active Antibody Mimic Based on an Antibody-Antigen Crystal Structure" *Am. Chem. Soc.* 116:2725-2733.

* cited by examiner

*Primary Examiner*—Celine Qian
(74) *Attorney, Agent, or Firm*—Knobbe Martens Olson & Bear LLP

(57) ABSTRACT

The present invention relates to an isolated mimetic of functional myostatin comprising part of the amino acid sequence of functional myostatin, such that the mimetic is capable of inhibiting muscle growth.

14 Claims, 4 Drawing Sheets

Figure 1: Purified Recombinant Myostatin

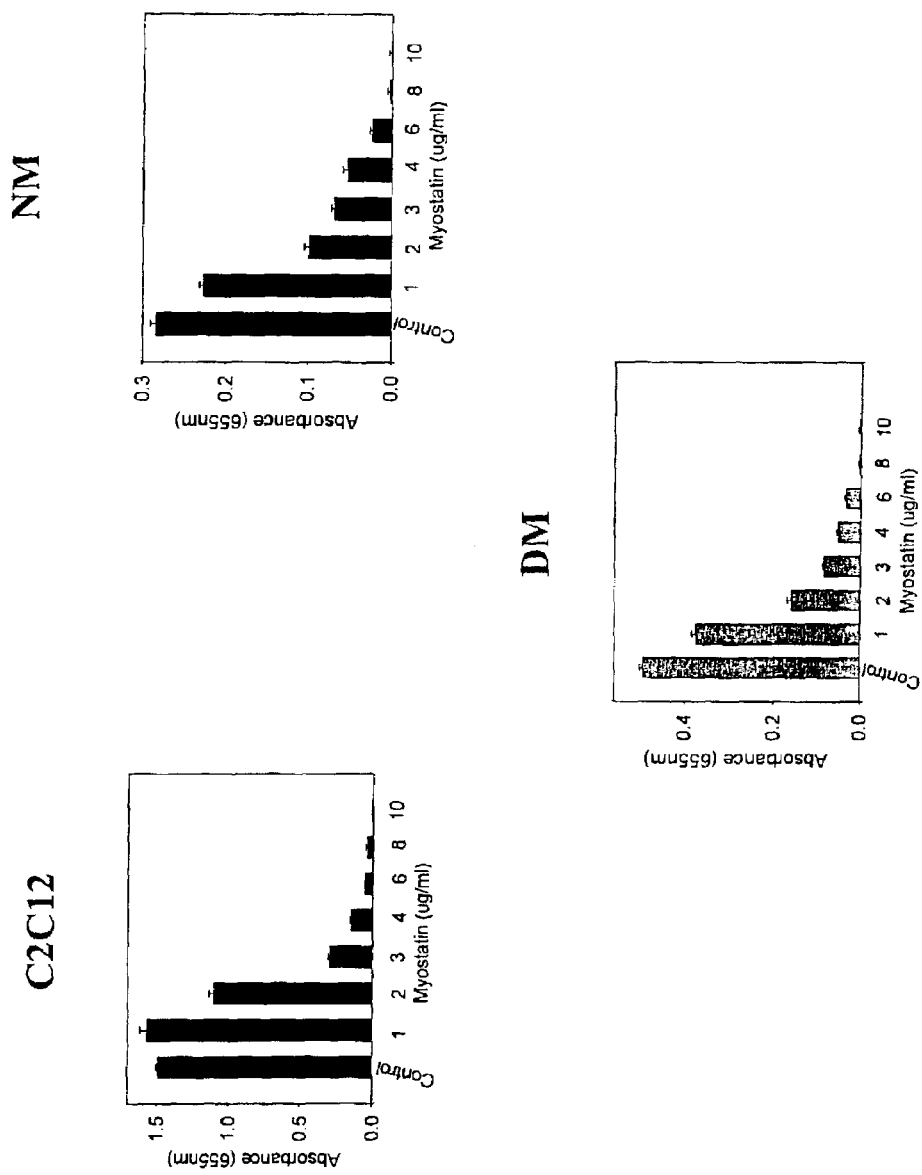

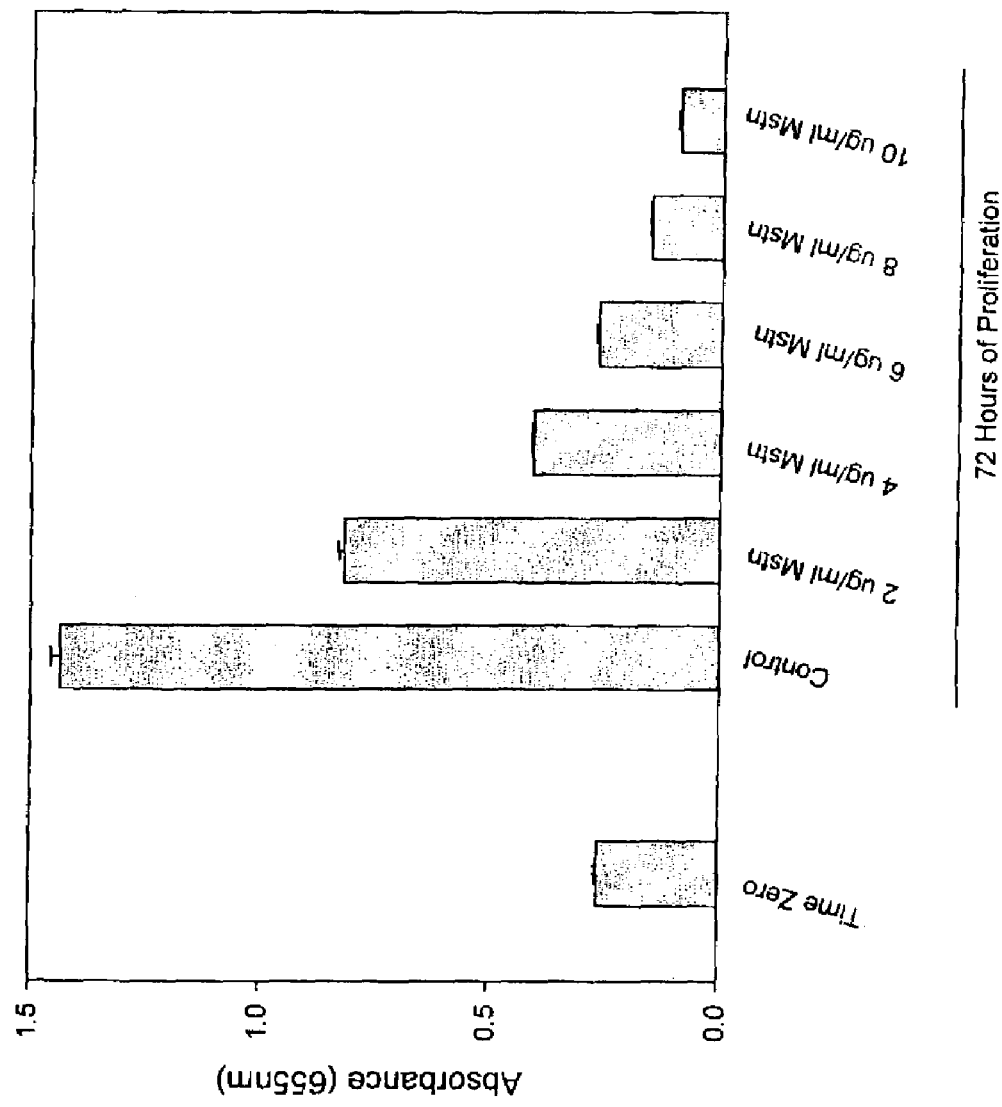

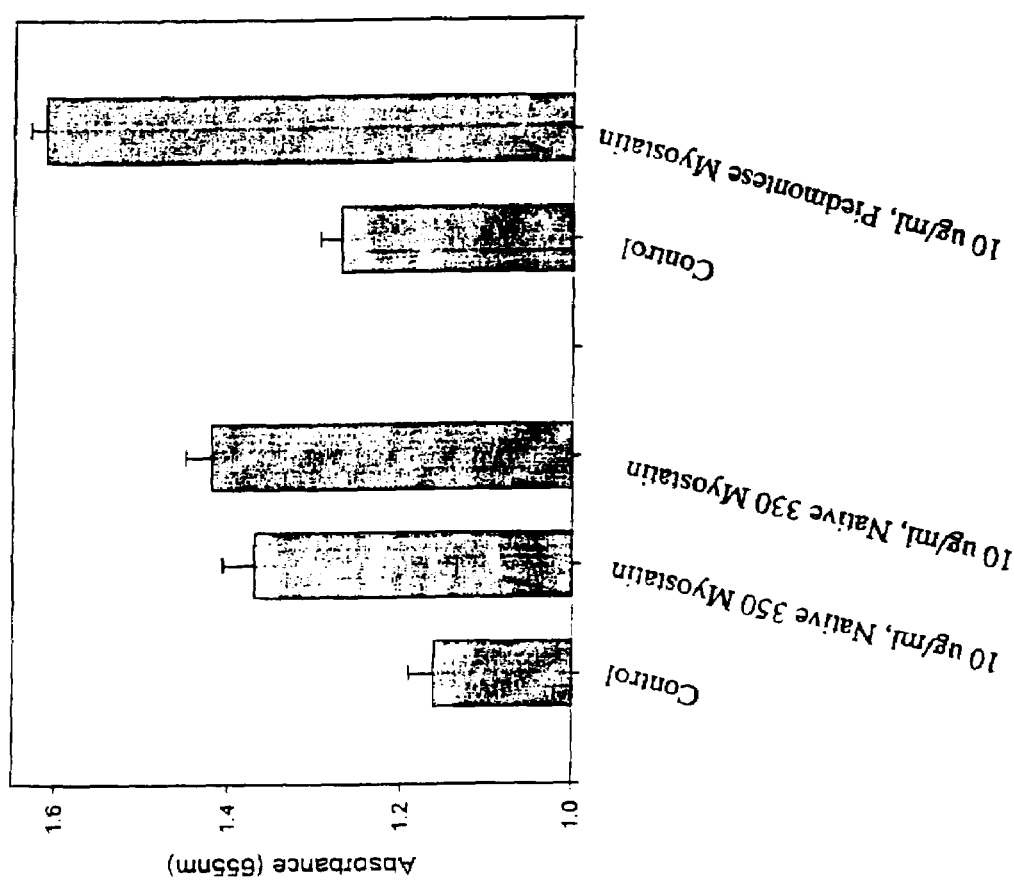

MYOSTATIN AND MIMETICS THEREOF

CROSS-REFERENCE TO RELATED APPLICATIONS

This is the U.S. National Phase under 35 U.S.C. §371 of International Application No. PCT/NZ01/00005, filed Jan. 18, 2001 and designating the United States and published in English, which claims priority to New Zealand Application No. 502389, filed Jan. 18, 2000.

This invention relates to myostatin, particularly, although by no means exclusively, to mimetics for functional myostatin and non-functional myostatin; their therapeutic use and to a method for identifying such mimetics.

BACKGROUND

All references, including any patents or patent applications, cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents forms part of the common general knowledge in the art, in New Zealand or in any other country.

Myostatin (MSTN) is a recently discovered member of the TGF beta super-family. Myostatin mRNA and protein have been shown to be expressed in skeletal muscle, heart and mammary gland. Targeted disruption of the myostatin gene in mice and a mutation in the third exon of myostatin gene in double-muscled Belgian Blue cattle, where a non-functional myostatin protein is expressed, leads to increased muscle mass. Hence myostatin has been shown to be a negative regulator of skeletal muscle growth.

The transforming growth factor-(TGF-β) superfamily of genes encode secreted factors that are important for regulating embryonic development and tissue homeostasis in adults. McPherron et al., (1997) described myostatin for the first time as being expressed specifically in developing and adult skeletal muscle and functioning, as discussed above, as a negative regulator of skeletal muscle mass in mice. Recent reports suggest that myostatin expression is not specific for skeletal muscle and that expression of myostatin is seen at least in heart and mammary gland, although studies reported in mouse, cattle and pigs have indicated that high levels of myostatin are detected specifically in developing and adult skeletal muscles (Kambadur et al., 1997; McPherron et al., 1997; Shaoquan et al 1998). Initially myostatin gene expression is detected in myogenic precursor cells of the myotome compartment of developing somites, and the expression is continued in adult axial and paraxial muscles (McPherron et al., 1997). Furthermore it was also shown that different axial and paraxial muscles expressed different levels of myostatin (Kambadur et al., 1997).

Myostatin null mice show a dramatic and widespread increase in skeletal muscle mass due to an increase in number of muscle fibres (hyperplasia) and thickness of fibres (hypertrophy) (McPherron et al., 1997). Subsequently, the present inventors (Kambadur et al., 1997) and others (McPherron and Lee, 1997; Grobet et al., 1997) reported that the Belgian Blue and Piedmontese breeds of cattle, which are characterized by an increase in muscle mass (double-muscling), have mutations in the myostatin coding sequence. This data suggests that somehow myostatin is a genetic determinant of skeletal muscle mass, and that myostatin is a negative regulator of muscle growth.

The molecular mechanism of action of myostatin is not known. The TGF beta proteins generally are synthesized as inactive precursor proteins, and at some point during the secretion the precursor protein is proteolytically processed and the processed mature protein is secreted. Two molecules of circulating processed protein together form a homodimer with "cysteine knot" structure, which elicits biological function by binding to its respective receptor. It would be desirable to understand the functions of myostatin at the molecular level in order to understand its biological action more fully, and to enable mimetics of both normal and mutated myostatin to be identified and used as therapeutic agents.

It is an object of the present invention to go some way towards achieving these goals, or at least to provide the public with a useful choice.

SUMMARY OF THE INVENTION

The present invention provides mimetics of functional myostatin, ie skeletal muscle growth inhibitors, and mimetics of non-functional myostatin, ie skeletal muscle growth promoters.

According to one aspect of the present invention there is provided an isolated mimetic of functional myostatin comprising part of the amino acid sequence of functional myostatin, such that the mimetic is capable of, of inhibiting muscle growth.

According to another aspect of the present invention there is provided an isolated mimetic of non-functional myostatin comprising part of the amino acid sequence of functional or non-functional myostatin, such that the mimetic is capable of promoting muscle growth.

Such mimetics preferably comprise part of the amino acid sequence of a functional or non-functional myostatin protein which binds to the Retinoic acid X Receptor and/or other myostatin receptor.

The inventors have shown for the first time that normal myostatin acts at the molecular level by binding to the Retinoic acid X Receptor (RXR). The most preferred mimetics therefore comprise peptides which bind to the RXR and/or other myostatin receptors.

The most preferred growth promoter mimetics comprise the truncated alleles MSTN 350, MSTN 330 as described herein.

It is to be clearly understood that the invention also encompasses peptide analogues, which include but are not limited to the following:

1. Compounds in which one or more amino acids is replaced by its corresponding D-amino acid. The skilled person will be aware that retroinverso amino acid sequences can be synthesised by standard methods; see for example Choreo and Goodman, 1993;
2. Peptidomimetic compounds, in which the peptide bond is replaced by a structure more resistant to metabolic degradation. See for example Olson et al, 1993; and
3. Compounds in which individual amino acids are replaced by analogous structures for example, gem-diaminoalkyl groups or alkylmalonyl groups, with or without modified termini or alkyl, acyl or amine substitutions to modify their charge.

The use of such alternative structures can provide significantly longer half-life in the body, since they are more resistant to breakdown under physiological conditions.

Methods for combinatorial synthesis of peptide analogues and for screening of peptides and peptide analogues are well known in the art (see for example Gallop et al, 1994; Hogan, 1997).

For the purposes of this specification, the term "peptide and peptide analogue" includes compounds made up of units which have an amino and carboxy terminus separated in a 1,2, 1,3, 1,4 or larger substitution pattern. This includes the 20 naturally-occurring or "common" α-amino acids, in either the L or D configuration, the biosynthetically-available or "uncommon" amino acids not usually found in proteins, such as 4-hydroxyproline, 5-hydroxylysine, citrulline and ornithine; synthetically-derived αamino acids, such as α-methylalanine, norleucine, norvaline, C.- and N-alkylated amino acids, homocysteine, and homoserine; and many others as known in the art.

It also includes compounds that have an amine and carboxyl functional group separated in a 1,3 or larger substitution pattern, such as β-alanine, γ-amino butyric acid, Freidinger lactam (Freidinger et al, 1982), the bicyclic dipeptide (BTD) (Freidinger et al, 1982; Nagai and Sato, 1985), amino-methyl benzoic acid (Smythe and von Itzstein, 1994), and others well known in the art. Statine-like isosteres, hydroxyethylene isosteres, reduced amide bond isosteres, thioamide isosteres, urea isosteres, carbamate isosteres, thioether isosteres, vinyl isosteres and other amide bond isosteres known to the art are also useful for the purposes of the invention.

A "common" amino acid is a L-amino acid selected from the group consisting of glycine, leucine, isoleucine, valine, alanine, phenylalanine, tyrosine, tryptophan, aspartate, asparagine, glutamate, glutamine, cysteine, methionine, arginine, lysine, proline, serine, threonine and histidine. These are referred to herein by their conventional three-letter or one-letter abbreviations.

An "uncommon" amino acid includes, but is not restricted to, one selected from the group consisting of D-amino acids, homo-amino acids, N-alkyl amino acids, dehydroamino acids, aromatic amino acids (other than phenylalanine, tyrosine and tryptophan), ortho-, meta- or para-aminobenzoic acid, ornithine, citrulline, norleucine, •-glutamic acid, aminobutyric acid (Abu), and α-α disubstituted amino acids.

The present invention further provides a method of decreasing skeletal muscle mass in an animal, comprising administering to said animal a muscle growth inhibiting amount of at least one growth inhibitor mimetic according to the invention.

The present invention further provides a method of increasing skeletal muscle mass in an animal, comprising administering to said animal a muscle growth promoting amount of at least one growth promoter mimetic according to the invention.

The present invention further provides a method of inhibiting the growth of cancerous myosarcoma cells, such as rhabdomyosarcomas, comprising administering to said cells a growth inhibiting amount of at least said growth inhibitor mimetic according to the invention.

According to a further aspect the present invention provides a method of identifying a molecule capable of modulating the activity of a myostatin receptor, comprising the steps of:
a) assessing the ability of a candidate molecule to compete with binding of wild-type [functional or non-functional] myostatin to the RXR or other myostatin receptor(s), or
b) assaying a candidate molecule in vitro or in vivo for ability to inhibit or promote muscle growth.

The present invention also provides for a non-human animal having increased muscle mass, produced by any of the aforementioned methods of the present invention.

According to another aspect, the present invention also provides the use of the functional myostatin protein, or mimetic thereof, in the manufacture of a pharmaceutical or veterinary composition for inhibiting the proliferation of myosarcomas.

According to yet a further aspect, the present invention also provides the use of functional myostatin protein, or a mimetic thereof, in the manufacture of a pharmaceutical composition for inhibiting the proliferation of rhabdomyosarcomas in a human or in a non-human animal, with the proviso that the muscle growth of said animals is regulated by myostatin.

According to still a further aspect, the present invention provides for a method for treating myosarcomas in a human or non-human animal comprising the step of administering to said human or non-human animal an effective amount of functional myostatin protein, or a mimetic thereof.

The Present invention also provides a computer-based method for identifying compounds which would have the desired structure to bind to a myostatin receptor, said method comprising the step of using three-dimensional structure software to compare known compounds with compounds known to bind to the receptor and/or for de novo design of new compounds capable of binding to the receptor.

It should be appreciated that throughout this specification the terms "growth inhibitor"; "growth promoter"; "muscle growth" and "muscle growth inhibition", or words to that effect, all refer to growth of skeletal muscle.

Throughout this specification the term "mimetic" refers to a molecule which because of its structural properties is capable of mimicking the biological function of either functional myostatin or non-functional myostatin.

Throughout this specification the term "functional myostatin" refers to a normal (i.e. non-mutated) myostatin protein which binds to RXR and/or to other myostatin receptor(s), and inhibits muscle growth, ie acts as a muscle growth inhibitor.

Throughout this specification the term "non-functional myostatin" refers to a mutated myostatin protein, such as Piedmontese protein, which binds to RXR and/or to other myostatin receptor(s), but does not inhibit muscle growth, ie acts as a muscle growth promoter.

Throughout this specification the term "other myostatin receptor(s)" refers to any one of the following three types of receptors to which members of the TGF-β superfamily of proteins are known to bind, namely:
(i) TGF-β receptor;
(ii) Activin receptor; and
(iii) Bone Morphogenetic Protein (BMP) receptor;

provided that binding of functional or non-functional myostatin or mimetics thereof results in either muscle growth promotion or muscle growth inhibition.

The RXR receptor and the "other myostatin receptor(s)" are collectively referred to herein as "myostatin receptors".

The inventors have found that myostatin binds to the RXR receptor. The binding domain of the myostatin protein is located in the region of amino acid residues 267-375 of the myostatin amino acid sequence.

In general, the mimetics of the present invention are prepared in an isolated, substantially pure form. In preferred embodiments the mimetics are at least 80% to 90% pure, and most preferably the mimetics are at least 99% pure.

The animal may be a human, or may be a domestic or companion animal, with the proviso that the muscle growth of said animal is regulated by myostatin. While it is particularly contemplated that the compounds of the invention are suitable for use in medical treatment of humans, they are also applicable to veterinary treatment, including treatment of companion animals such as dogs and cats; and domestic animals such as horses, cattle, sheep, pigs, goats, deer and poultry, or zoo animals such as felids, canids, bovids, and ungulates.

Methods and pharmaceutical carriers for preparation of pharmaceutical compositions are well known in the art, as set out in textbooks such as Remington's Pharmaceutical Sciences, 19th Edition, Mack Publishing Company, Easton, Pa., USA.

The compounds and compositions of the invention may be administered by any suitable route, and the person skilled in the art will readily be able to determine the most suitable route and dose for the condition to be treated. Dosage will be at the discretion of the attendant physician or veterinarian, and will depend on the nature and state of the condition to be treated, the age and general state of health of the subject to be treated, the route of administration, and any previous treatment which may have been administered.

The carrier or diluent, and other excipients, will depend on the route of administration, and again the person skilled in the art will readily be able to determine the most suitable formulation for each particular case.

For the purposes of this specification it will be clearly understood that the word "comprising" means "including but not limited to", and that the word "comprises" has a corresponding meaning.

DETAILED DESCRIPTION OF THE INVENTION

The present invention describes a bioassay for myostatin. Using this assay the inventors provide a means for identifying a mimetic of functional myostatin, ie a skeletal muscle growth inhibitor, comprising a part of the amino acid sequence of the functional myostatin protein, which will bind to myostatin receptors.

Growth inhibitor mimetics will act as ligands of the myostatin receptors in one or more in vitro or in vivo biological assays of myostatin activity.

One example of an in vitro biological assay of myostatin activity is the inhibition of proliferation of cultured myoblasts. The addition of an effective amount of at least one growth inhibitor mimetic of the invention will inhibit the proliferation of the myoblasts.

One example of an in vivo biological assay of myostatin activity is the reduction of the muscle mass in either normal or in myostatin null mice. The administration thereto of an effective amount of at least one growth inhibitor mimetic of the present invention will result in a reduction of muscle mass in the test animals.

Preferred growth inhibitor mimetics are peptides comprising the entire length of, or a part of the functional myostatin protein.

The present invention further provides mimetics of non-functional myostatin (Piedmontese allele), i.e. muscle growth promoters, comprising a part of the amino acid sequence of the functional or non-functional myostatin protein.

Without wishing to be limited by any proposed mechanism, it is hypothesised that the growth promoter mimetics act as dominant negatives. Since the mutant myostatin is present in multimolar excess, it can out-compete wild-type myostatin and form heterodimers with the wild-type molecules, and thereby act as dominant negative of the biological function of myostatin.

Such growth promoter mimetics will act as antagonists of myostatin action in one or more in vitro or in vivo biological assays of myostatin activity.

One example of an in vitro biological assay of such growth-promoting myostatin mimetic activity is the enhancement of proliferation of cultured myoblasts by the addition thereof of an effective amount of at least one growth- promoter mimetic of the present invention.

One example of an in vivo biological assay of such growth-promoting myostatin mimetic activity is the enhancement of skeletal muscle mass in normal mice or other test animal by administration to of an effective amount of at least one growth-promoter mimetic of the present invention.

The present invention further provides a method for identifying molecules:

(a) which will bind to the retinoic acid X receptor (RXR) or other myostatin receptor(s), and act as functional myostatin mimetics (muscle growth inhibitors), or (b) which compete with binding of normal myostatin to the RXR, and act as nonfunctional myostatin mimetics (muscle growth promoter), in which said method comprises the step of conducting an in vitro or in vivo assay for muscle growth inhibition or promotion.

The method involves the use of one or more in vitro or in vivo assays of myostatin activity. For example, mimetic molecules should be able either to inhibit myoblast proliferation in culture (growth inhibitor mimetic) or to enhance myoblast proliferation in culture (growth promoter mimetic) as described above.

Potential mimetics can also be identified in animal models, which can include cows, sheep, pigs, poultry or rodents.

A potential growth inhibitor mimetic may be identified, for example, by using a myostatin null mouse which has an increased muscle mass. In this assay, a potential growth inhibitor mimetic is administered to the myostatin null mouse and reduction of the increased muscle mass is measured. A reduction in muscle mass indicates that a candidate mimetic is inhibiting muscle cell proliferation.

Similarly a potential growth promoter mimetic may be identified by administering it to a normal mouse and then measuring the effect on muscle mass. An increase in muscle mass indicates that a candidate mimetic is enhancing muscle cell proliferation and acting as a dominant negative form of myostatin.

These are just a few examples of suitable assays. Other assays for myostatin activity known to those skilled in the art may also be used.

Potential mimetics may be identified using a computer-based method for identifying compounds which would have the desired structure to bind to the RXR using three dimensional structure software, said method utilising the software for the step(s) of: comparison of known compounds with compounds known to bind to RXR, and/or for de novo design for new compounds capable of binding to RXR, or other myostatin receptors. Suitable programs will be known to persons skilled in the art. Examples of suitable computer programs include The Modeller by Rockefeller University and The SWISS Model developed by Swiss Protein database.

It will be appreciated that the above computer-based method can also be used to identify compounds having the desired structure to bind to other myostatin receptor(s).

Potential mimetics identified by such computer-based methods may then be tested for activity in the above described biological assays.

The present invention also provides for molecules identified by any of the aforementioned methods of the present invention.

The present invention further provides a method of increasing muscle mass in an animal which comprises administering to said animal an effective amount of at least one growth promoter mimetic according to the invention. It should be appreciated that the animals to which the present invention relates are only those which have their muscle growth regulated by myostatin. Consequently, animals whose muscle growth is not regulated by myostatin are not intended to fall within the scope of the present invention.

Also contemplated by the present invention is a composition comprising an effective amount of at least one growth promoter mimetic according to the invention, together with a pharmaceutically or veterinarily acceptable carrier.

Preferably the composition comprises MSTN 350 and/or MSTN 330, together with a pharmaceutically acceptable carrier.

The present invention further provides a method of increasing muscle mass in an animal, comprising:
(i) developing a transgenic non-human animal by the insertion of a gene construct comprising the coding sequence for at least one growth promoter mimetic of the invention operatively linked to suitable promoter and/or enhancer sequences to drive transcription thereof, and delivering said construct to a somatic cell, followed by nucleic and embryo transfer, or by injecting said gene construct into a one cell embryo followed by embryo transfer to produce a transgenic non-human animal;
(ii) injecting a gene construct comprising the coding sequence for at least one growth promoter mimetic as described herein into skeletal muscle or other appropriate tissue of an animal;
(iii) transfecting skeletal muscle or other appropriate tissue with a gene construct comprising the coding sequence for at least one growth promoter mimetic as described herein using a chemically-mediated technique; or(iv) administration of an effective amount of a recombinant myostatin mimetic to an animal.

For example, the transgenic animal may be generated by the insertion of a gene construct comprising the coding sequence for at least one growth promoter mimetic of the invention, operatively linked to suitable promoter and/or enhancer sequences to drive transcription thereof, and delivering said construct to a somatic cell, followed by nucleic and embryo transfer, or by injecting said gene construct into a one cell embryo followed by embryo transfer to produce a transgenic non-human animal. In alternative (iv), the mimetic may be administered by any suitable route.

Thus the present invention contemplates increasing muscle mass for increasing meat production of farm animals, as well as in the treatment of muscle-wasting diseases in humans.

The invention therefore provides a method of increasing skeletal muscle mass in transgenic animals. By over expression of a gene cassette comprising a DNA sequence encoding at least one growth promoter mimetic according to the invention, operatively linked to a suitable promoter which expresses in skeletal muscle or to the myostatin promoter, skeletal muscle mass may be increased. This cassette would also contain 3' flanking DNA that could stabilise the mRNA, and may contain downstream regulatory sequences. This DNA cassette could be introduced into the genome of mammals by microinjection of the DNA into the pronuclei of eggs (as described in L'Huillier et al PNAS 93; 6698-6703), which are subsequently transferred back to recipient animals and allowed to develop to term. This technique for the production of transgenic animals is described by Hogan et al (1996; In: "Manipulating the mouse embryo", Cold Spring Harbor Laboratory Press). Another way to produce transgenic animals would involve transfection of cells in culture that are derived from an embryo, or from foetal or adult tissues, followed by nuclear transfer and embryo transfer to recipient animals, or the gene cassette may be bound to mammalian sperm and delivered to the egg via in vitro or in vivo fertilisation to produce a non-human transgenic animal.

Increasing muscle mass may also be accomplished by gene therapy techniques, whereby said gene cassette is injected into the skeletal muscle or appropriate tissue of an animal or human in vivo or by transfection of the skeletal muscle cells or appropriate tissue using chemically-mediated transfection techniques such as liposome reagents which bind to the DNA and facilitate cellular uptake of the gene cassette.

BRIEF DESCRIPTION OF DRAWINGS

The invention will now be exemplified with reference to the accompanying drawings, in which FIG. 1 Shows a Coomassie blue stained SDS-Polyacrylamide gel picture of purified myostatin. Molecular weight in Kilodaltons is shown next to the protein molecular weight markers (MWM). The protein band corresponding to the purified processed myostatin is indicated by the arrow.

FIG. 2 Shows the results of a myoblast proliferation assay for myostatin. Three different cell lines including mouse C2C12 cells and the bovine myoblasts isolated for normal muscle (NM) and double-muscled (DM) Belgian Blue cattle are used for the assay. The proliferation of myoblasts is measured by methylene blue assay and the optical density at 655 nm is shown on the Y axis. Varying concentrations of myostatin used in each assay is shown on the X axis.

FIG. 3 Shows the results of a proliferation assay for myostatin for rhabdomyosarcoma (RD) cells. The optical density of surviving RD cells at 655 nm is shown on the Y axis. Varying concentrations of myostatin treatment for 72 in each assay is shown on the X axis. The cell density at time zero is also shown.

FIG. 4 Shows the effect of the three dominant-negative myostatin alleles (350, 330 and Piedmontese) on the proliferation of myoblasts.

EXPRESSION AND PURIFICATION OF MYOSTATIN PROTEIN

Figure 1:
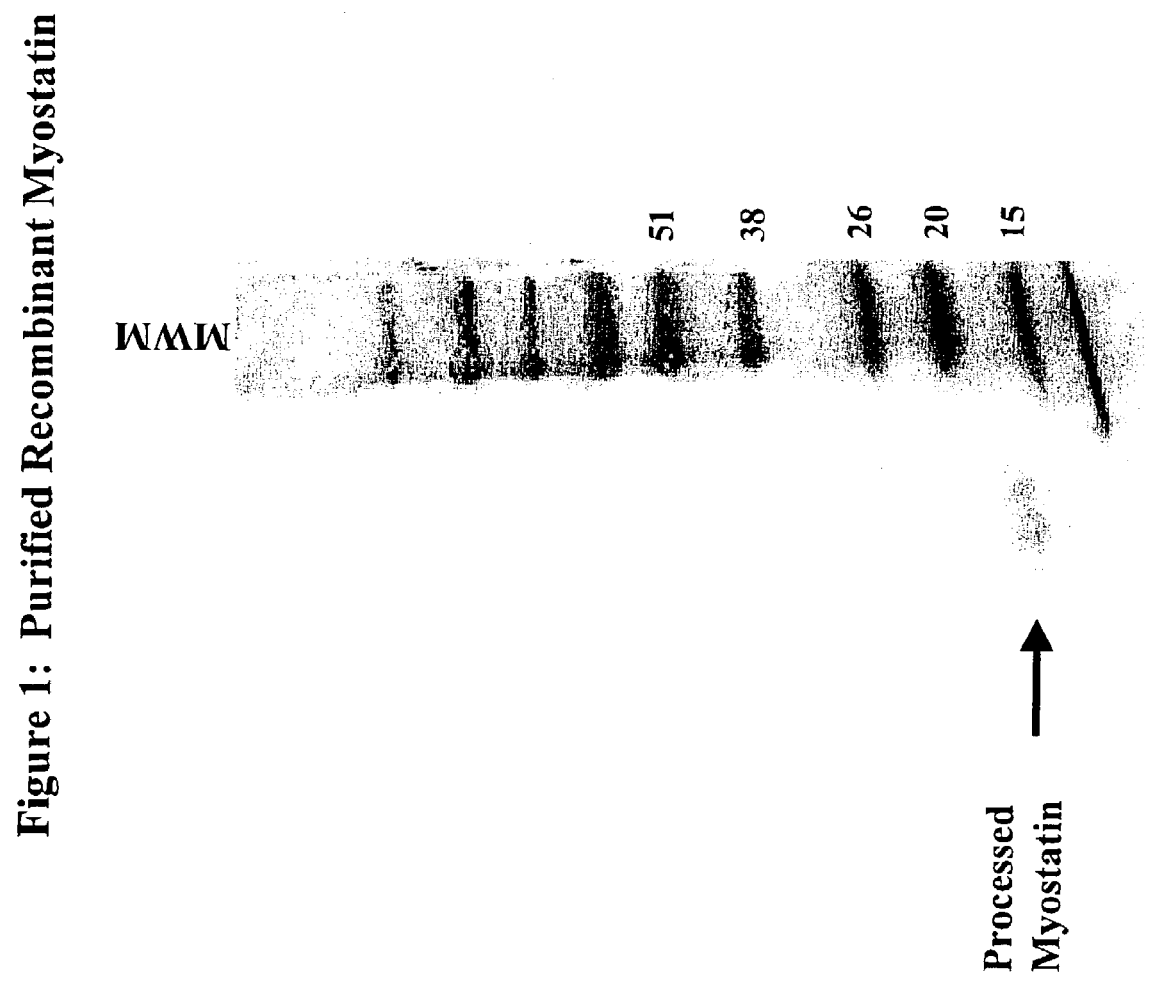

Myostatin protein is synthesized and processed at a conserved RSRR(263-266) site to give mature myostatin, which is biologically active (Sharma et al 1999). Hence we used the pET system to express this processed portion of myostatin (267-375) and its variants (267-350 and 267-330) as N-terminal histidine fusion proteins in *E. coli*. The expressed histidine fusion proteins were purified on a Ni-Agarose column and separated on SDS-gel to check for the purity. As shown in FIG. 1, Coomassie blue staining revealed that a single myostatin fusion protein band around ~15 kDa was present in the eluted fractions. Furthermore, the purified myostatin and its variants (350 MSTN and 330 MSTN) appear to be highly purified after single step purification.

Myostatin Inhibits the Proliferation of Myoblasts and Rhabdomyosarcoma Cells

Since mutations in Myostatin lead to hyperplasia of muscle, we investigated whether an underlying mechanism for negative regulation of muscle growth by myostatin operates through regulating the proliferation rate of myoblasts. For this purpose we have used C2C12 transformed myoblasts and primary cultures of bovine myoblasts from both normal and double-muscled Belgian Blue animals, which carry a mutation in the myostatin gene. To determine the effect of increased myostatin protein concentration on the proliferation of myoblasts, we cultured myoblasts in the presence of varying concentration of myostatin, and evaluated the proliferation of myoblasts by methylene blue assay. When C2C12 myoblast cells were treated with myostatin at a concentration of 2 µg/ml for 72 hours, there was only slight inhibition of myoblast proliferation (FIG. 2). Inhibition of C2C12 cell proliferation was found to be 100% at 10 µg/ml myostatin over 72 hours of treatment in serum-supplemented medium (FIG. 2). Similarly, when purified bovine myoblast cultures were incubated with either 2 or 10 µg/ml concentration of myostatin, the inhibition was observed to be 60 or 100% over 72 hours (FIG. 2). When purified myoblasts from double-muscled Belgian Blue animals were incubated with 10 µgs/ml of recombinant myostatin for 72 hours, there was 100% inhibition of myoblast proliferation.

When rhabdomyosarcoma cells were incubated with 2-10 µgs/ml of myostatin in serum supplemented media, there was 50% inhibition of growth of rhabdomyosarcoma cells at 2 µg/ml of myostatin. Ten µg/ml concentration of myostatin resulted in 100% growth inhibition of rhabodomyocarcoma cells (FIG. 3).

C-terminal Truncations and Piedemontise Myostatin Allele Act as Dominant Negatives To isolate and characterise the dominant negative forms of myostatin, we produced truncated myostatin protein and protein with the Piedmontese allele in *E. coli* and purified the proteins on a Ni-agarose column. Exponentially growing myoblast cultures were incubated with either the purified trunctated 350 MSTN or 330 MSTN or Piedemontese protein as described above. As shown in FIG. 4, no inhibition in the proliferation of myoblasts was observed at any concentration when actively growing myoblasts were incubated with either 350 MSTN, 330 MSTN or Piedemontese allele. In contrast, enhanced proliferation of myoblasts was observed in the presence of the mutated myostatin proteins, indicating that these three mutant alleles act as dominant negatives for myostatin function.

Isolation of Myostatin Receptor

To isolate the myostatin receptor, the Lex-A yeast two hybrid system was used Gyuris et al (1975). Mature myostatin was used as bait to screen a skeletal muscle cDNA library to recover several clones that coded for myostatin interacting proteins. Sequencing of these clones revealed that myostatin specifically interacted with Retinoic X receptor, thus indicating that myostatin binds to RXR receptor.

It should be appreciated that throughout this specification wherever the term "comprises" (or grammatical variants thereof) is used, this term is not intended to be limiting and it does not exclude the presence of other features or elements in the present invention. Thus, the word "comprises" is equivalent to the word "includes".

Aspects of the present invention have been described by way of example only, and it should be appreciated that modifications and additions may be made thereto without departing from the scope thereof as defined in the appended claims.

REFERENCES

Choreo and Goodman, Acc. Chem. REs., 1993 26 266-273

Freidinger, R. M., Perlow, D. S., Veber, D. F., J. Org. Chem. 1982, 59, 104-109

Gallop, M. A., Barrett, R. W., Dower, W. J., Fodor, S. P. A. and Hogan, Jr., J. C. Nature Biotechnology,1997 15 328-330.

Nagai, U., Sato, K. Tetrahedron Lett. 1985, 26, 647-650.

Olson et al., J. Med. Chem., 1993 36 3039-3049.

Smythe, M. L., von Itzstein, M., J. Am. Chem. Soc. 1994, 116, 2725-2733

Grobet L, Martin L J, Poncelet D, Pirottin D, Brouwers B, Riquet J, Schoeberlein A, Dunner S, Menissier F, Massabanda J, Fries R, Hanset R & Georges M 1997 A deletion in the bovine myostatin gene causes the double-muscled phenotype in cattle. Nat Genet 17 71-74.

Gyuris J, Golemis E, Chertkov H, Brent R & 1975 (4):791-803. N 1993 Cdil, a human G1 and S phase protein phosphatase that associates with Cdk2. Cell 75 791-803.

Hogan B, Beddington R, Costantini F & Lacey E 1986 Manipulating the Mouse Embryo.

Ji S, Losinski R L, Cornelius S G, Frank G R, Willis G M, Gerrard D E, Depreux F F & Spurlock M E 1998 Myostatin expression in porcine tissues: tissue specificity and developmental and postnatal regulation. Am J Physiol 275 R1265-1273.

Kambadur R, Sharma M, Smith T P & Bass J J 1997 Mutations in myostatin (GDF8) in double-muscled Belgian Blue and Piedmontese cattle. Genome Res 7 910-916.

L'Huillier P J, Soulier S, M-G. S, Lepourry L, Davis S R, Mercier J-C & Vilotte J-L 1996 Efficient and specific ribozyme-mediated reduction of bovine -lactalbumin expression in double transgenic mice. PNAS 93 6698-6703.

McPherron A C, Lawler A M & Lee S J 1997 Regulation of skeletal muscle mass in mice by a new TGF-beta superfamily member. Nature 387 83-90.

McPherron A C & Lee S J 1997 Double muscling in cattle due to mutations in the myostatin gene. Proc Natl Acad Sci USA 94 12457-12461.

Sharma M, Kambadur R, Matthews K G, Somers W G, Devlin G P, Conaglen J V, Fowke P J & Bass J J 1999 Myostatin, a transforming growth factor-beta superfamily member, is expressed in heart muscle and is upregulated in cardiomyocytes after infarct. J Cell Physiol 180 1-9.

What we claim is:

1. An isolated polypeptide capable of promoting muscle growth, comprising a mature myostatin peptide of amino acids 267 to 375 of myostatin amino acid sequence, wherein C-terminus is truncated at amino acid positions 330 or 350.

2. The polypeptide of claim 1, wherein the C-terminus is truncated at amino acid position 330.

3. The polypeptide of claim 1, wherein the C-terminus is truncated at amino acid position 350.

4. A composition comprising an effective amount of the polypeptide as claimed in any one of claims 2 or 3, together with a pharmaceutically or veterinarily acceptable carrier.

5. A composition comprising an effective amount of at least one polypeptide capable of promoting muscle growth, said polypeptide comprising a mature myostatin peptide of amino acids 267-375 of myostatin amino acid sequence, wherein C-terminus is truncated at amino acid positions 330 or 350.

6. A method for increasing the muscle mass in an animal after an injury, which comprises administering to said animal an effective amount of at least one growth promoter mimetic according to claim 1.

7. The method of claim 6, wherein the animal is selected from the group consisting of: companion animals; domestic animals, and zoo animals.

8. The method of claim 7, wherein said companion animals are dogs and cats; said domestic animals are horses, cattle, pigs, goats, deer, sheep, and poultry; and said zoo animals are felids, canids, bovides and ungulates.

9. The method of claim 6, wherein the animal is a human.

10. A method for increasing muscle mass of a non-human animal after an injury, comprising administering to said non-human animal the composition of claim 4.

11. The method of claim 10, wherein said non-human animal is selected from the group consisting of companion animals, domestic animals, and zoo animals.

12. The method of claim 11, wherein said companion animal is a dog or a cat.

13. The method of claim 11, wherein said domestic animal is selected form the group consisting of horses, cattle, pigs, goats, deer, sheep, and poultry.

14. The method of claim 11, wherein said zoo animal is selected from the group consisting of canids, bovides and ungulates.

* * * * *

UNITED STATES PATENT AND TRADEMARK OFFICE
CERTIFICATE OF CORRECTION

| | |
|---|---|
| PATENT NO. | : 7,368,534 B2 |
| APPLICATION NO. | : 10/181545 |
| DATED | : May 6, 2008 |
| INVENTOR(S) | : Bass et al. |

It is certified that error appears in the above-identified patent and that said Letters Patent is hereby corrected as shown below:

On the Title page, left column under item (30) Foreign Application Priority Data, please delete "Jan. 18, 2001" and insert --Jan. 18, 2000--, therefore.

On the Title page, right column under item (56) Other Publications, at line 34, please delete "Sahpe" and insert --Shape--, therefore.

At column 3, line 13, please delete "αamino" and insert --α-amino--, therefore.

At column 6, line 65, please delete "Rockerfeller" and insert --Rockefeller--, therefore.

At column 9, line 33 (approx.), please delete "10 μgs/ml" and insert --10 μg/ml--, therefore.

At column 9, line 39, please delete "rhabodomyocarcoma" and insert --rhabdomyosarcoma--, therefore.

At column 9, line 42, please delete "Piedemontise" and insert --Piedmontese--, therefore.

At column 9, line 50, please delete "Piedemontese" and insert --Piedmontese--, therefore.

At column 9, line 54, please delete "Piedemontese" and insert --Piedmontese--, therefore.

In Claim 7, please delete "animals;" and insert --animals,--, therefore.

In Claim 8, please delete "bovides" and insert --bovids--, therefore.

In Claim 11, please delete "of" and insert --of:--, therefore.

UNITED STATES PATENT AND TRADEMARK OFFICE
CERTIFICATE OF CORRECTION

PATENT NO.         : 7,368,534 B2
APPLICATION NO.    : 10/181545
DATED              : May 6, 2008
INVENTOR(S)        : Bass et al.

It is certified that error appears in the above-identified patent and that said Letters Patent is hereby corrected as shown below:

In Claim 14, please delete "bovides" and insert --bovids--, therefore.

Signed and Sealed this

Tenth Day of March, 2009

JOHN DOLL
*Acting Director of the United States Patent and Trademark Office*